United States Patent [19]

Takahashi

[11] 4,303,342

[45] Dec. 1, 1981

[54] METHOD AND APPARATUS FOR DETECTING FOREIGN MATTERS IN LIQUIDS

[75] Inventor: Toshio Takahashi, Honjo, Japan

[73] Assignee: Eisai Co., Ltd., Tokyo, Japan

[21] Appl. No.: 126,615

[22] Filed: Mar. 3, 1980

[30] Foreign Application Priority Data

Mar. 8, 1979 [JP] Japan .................................. 54-27126

[51] Int. Cl.³ ............................................ G01N 21/90
[52] U.S. Cl. .................................... 356/427; 250/565; 356/442; 356/240
[58] Field of Search ........................ 356/240, 427, 442; 250/564, 565, 574

[56] References Cited

U.S. PATENT DOCUMENTS 3,777,169 12/1973 Walter et al. ........................ 356/240
3,966,332 6/1976 Knapp et al. ........................ 356/427
4,095,904 6/1978 Klein et al. .......................... 356/427

FOREIGN PATENT DOCUMENTS 2820661 11/1978 Fed. Rep. of Germany ...... 356/427

*Primary Examiner*—R. A. Rosenberger
*Attorney, Agent, or Firm*—Blanchard, Flynn, Thiel, Boutell & Tanis

[57] ABSTRACT

Method and apparatus for detecting foreign matters in liquids by irradiating light to a transparent container in which foreign matters are suspended and swirled together with the content liquid, and by measuring the change of transmitted light by individual units of a group of small light receivers. The change of transmitted light due to the displacement of the liquid surface is detected by the small light receivers, and the detection signals are taken up as DC components. In contrast, the change of transmitted light due to moving foreign matters is detected by the small light receivers, and the detection signals are taken up as AC components by means of capacitors. When the detection signal of the liquid surface is lower than the preset standard value, the small light receiver corresponding to the liquid surface is inhibited to issue an output, regardless of detection of foreign matters.

8 Claims, 5 Drawing Figures

METHOD AND APPARATUS FOR DETECTING FOREIGN MATTERS IN LIQUIDS

BACKGROUND OF THE INVENTION

The present invention relates to a method and apparatus for detecting solids and foreign matters that might be present in transparent containers filled with a liquid. More particularly, the present invention relates to an improved method and apparatus for detecting automatically such undesirable minute foreign matters as glass chips, fibers, and dust that might be present in such transparent, closed containers as vials, ampoules, and infusion solution bottles in which is filled a liquid, by measuring the change of transmitted light with a group of small light receivers, wherein the improvement comprising the means that eliminates from the detecting visual field the signals only from the swirling surface, which occurs when the object (such as ampoule) to be detected is rotated and then brought to a stop quickly, while following the swirling liquid level as it is restored gradually, whereby detection can be performed immediately after the stop of rotation, without waiting until the liquid surface becomes completely stationary, although the transmitted light is changed by the liquid surface.

Heretofore, a method as shown in FIG. 1 has been in use for detection of foreign matters. In this method, an ampoule (1) to be inspected is placed on a rotating device, turned at a high speed by motor (2), and then stopped quickly by a brake. Light from lamp (4) is irradiated to ampoule (1) through condenser lens (5) and a vertical slit (not shown) as indicated by chain lines. The irradiated light passes through the liquid and hits small light receivers $(7_1)$, $(7_2)$, . . . , $(7_n)$ constituting light detector (7), through image forming lens (6). The magnitude of transmitted light changes if there are foreign matters that are suspending and swirling with the content liquid. The presence of foreign matters is judged according to the extent of decrease of transmitted light.

Such a conventional method has a disadvantage that if the surface (8) of the content liquid coincides with the light receiving position, the light incident on that part becomes dim on transmission through the liquid surface, causing the small light receivers to receive extremely decreased light, and as the liquid surface moves up and down, the quantity of light incident upon the small light receiver fluctuates and this fluctuation is processed in the same manner as for the change in the quantity of light caused by foreign matters and the resulting signals are mistaken for the signals caused by foreign matters. In order to eliminate such a disadvantage, it is necessary to exclude the signals corresponding to the liquid surface (8) from the signals to be inspected. This has been accomplished in the conventional method by carrying out measurements while foreign matters are still suspended and swirled together with the content liquid after the swirl in the ampoule has become moderate and the liquid surface (8) has been restored to the upper level. This has still another disadvantage that heavy or relatively large foreign matters such as glass chips tend to settle as soon as the rotating ampoule is brought to a stop, and therefore they would have deposited on the bottom of the container (1) and would not be detected as foreign matters if measurement is carried out after the swirl has become moderate and the liquid surface (8) is restored.

The measurement is made more complex by the fact that the restoration of the swirling liquid surface (8) varies delicately depending on the viscosity of the content liquid, the quantity of the liquid filled, the shape and size of the container (1), the speed of rotation, and the timing of stop. There is variation among ampoules even for the same solution.

Therefore, the conventional method in which measurement is carried out sequentially from bottom to top according to a standardized, preset program, does not comply with the delicate ampoule to ampoule difference and tends to give incorrect results. In addition, the conventional method is inefficient if different programs are to be set for respective kinds of ampoules and liquids.

In order to obviate these disadvantages, we have completed this invention which is characterized by that the detection is accomplished as the liquid surface is restored, with the light receivers corresponding to the liquid surface being omitted in the detection.

A single photoelectric element is not suitable as a light detector which is to be used for the light receiver of the apparatus according to this invention. This is because foreign matters to be detected are extremely small as compared with the detecting visual field and the difference in the magnitude of photoelectric current which is caused by the presence of foreign matters is too small to detect foreign matters with reasonable sensitivity. A satisfactory detection with a sufficient S/N ratio can be accomplished for any kind of foreign matters, whatever shape they might be—particulate or fibrous, if we install a multiplicity of small light receivers, each having a certain light receiving area equal to or smaller than the projected area of individual particles of foreign matters and measure the intensity of the beam of passing light with the small light receivers which varies in proportion with the projected area of foreign matters.

According to the method of this invention, the swirling liquid surface in each ampoule is caught by the small light receivers of the light detector and output signals from the small light receivers corresponding to the swirling liquid surface are excluded from other signals for measurement, and thus continuous measurement is possible for individual ampoules even though the time for the swirling liquid surface to be restored differs depending on the viscosity of the liquid, the shape and size of the container, and the quantity of liquid filled in the container. Therefore, there is no need for setting programs, and effective, error-free measurement can be accomplished.

The light that has passed the liquid surface is extremely dimmed as compared with one that has passed the content liquid. Using this it is possible to inhibit the small light receivers corresponding to the liquid surface from issuing output signals and to permit the other small light receivers to issue digital output signals, if the signal from the small light receivers is lower than the arbitrarily set standard value. Signals from the small light receivers are filtered by capacitors to remove DC components and only signals due to moving foreign matters are taken up as AC components. Such signals are compared with the arbitrarily set standard value by comparators, and those signals exceeding such standard value are issued for defective ampoules. The output due to foreign matters and the output not corresponding to the liquid surface undergo AND operation to eliminate signals resulting from the liquid surface so that only output signals resulting from foreign matters are obtained as outputs that actuate the solenoid for removing defective ampoules.

Incidentally, in the method and apparatus of this invention, the detection visual field covers the upper part of the ampoule in which there is no liquid, but this has nothing to do with the detection of foreign matters because the light that passes the empty part is more intense than the light that passes the liquid and the intensity remains constant.

OBJECT OF THE INVENTION

As will be apparent from the above-mentioned, it is the object of this invention to provide a method and apparatus for inspecting transparent containers rapidly by rotating them one by one at a high speed and then bringing them to a stop quickly.

It is another object of this invention to provide a method and apparatus for inspecting transparent containers without setting different programs according to individual containers and liquids to be inspected.

These and other objects and advantages of this invention will be readily ascertained by referring to the following description and appended drawings.

Figure 1:
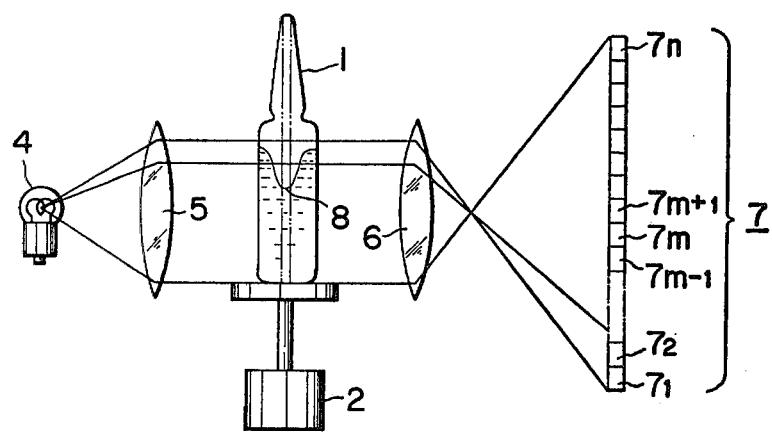
FIG. 1 is a schematic diagram showing the principle of the conventional apparatus for detecting foreign matters.

The invention will be described referring to the embodiments shown in the drawings.

Figure 2:
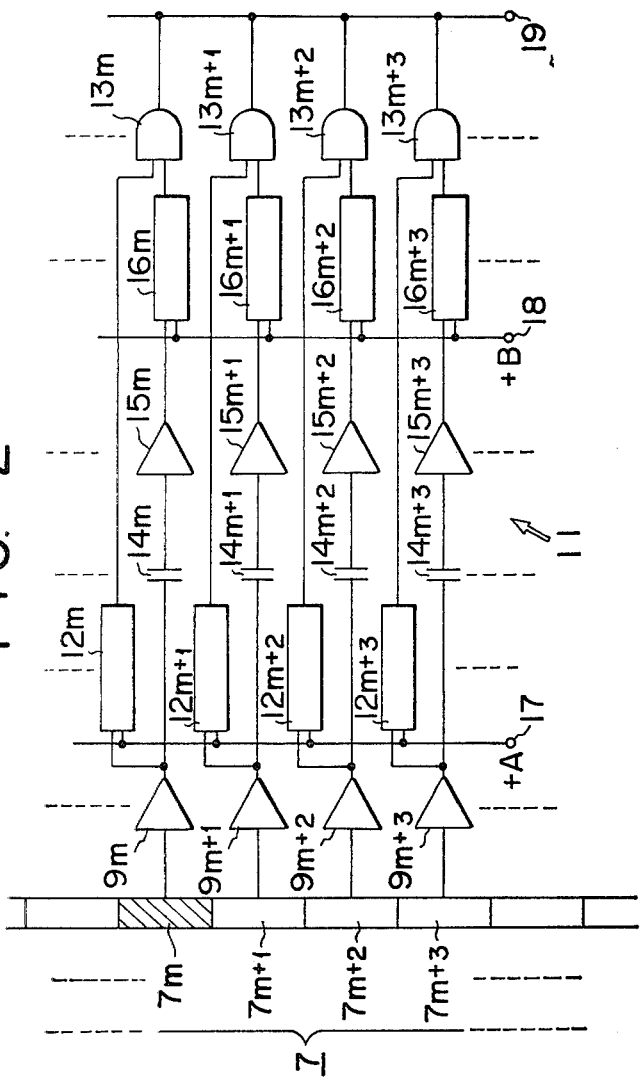
FIG. 2 is a block diagram showing the first embodiment of the apparatus according to this invention.

There is shown in FIG. 2 the light detector (7) which is an aggregate of small light receivers $(7_1)$, $(7_2)$, . . . , $(7_m)$, . . . , $(7_n)$, each of which is made up of a bundle of optical fibers such as glass fibers, each bundle having a cross sectional area of $10^{-2}$ to 1 mm$^2$, and a photoelectric element connected to one end thereof. The light receivers $(7_1)$, $(7_2)$, . . . , $(7_n)$ are connected respectively to amplifiers $(9_1)$, $(9_2)$, . . . , $(9_n)$ and further to first comparators $(12_1)$, $(12_2)$, . . . , $(12_n)$ that detect liquid surface (8) and circuit (11) that detects foreign matters. The circuit (11) to detect foreign matters is made up of capacitors $(14_1)$, $(14_2)$, . . . , $(14_n)$, amplifiers $(15_1)$, $(15_2)$, . . . , $(15_n)$, and second comparators $(16_1)$, $(16_2)$, . . . , $(16_n)$. The AND circuits $(13_1)$, $(13_2)$, . . . , $(13_n)$ inhibit signals for detection of foreign matters from being issued when the liquid surface is detected.

Now, how the circuit thus constructed works is described. The liquid surface (8) forms a swirl in conical shape as the ampoule is turned. The light that has passed this liquid surface is much more dimmed than the one that has passed the liquid straight. The outputs of light receivers $(7_1)$, $(7_2)$, . . . , $(7_n)$ are amplified by amplifiers $(9_1)$, $(9_2)$, . . . , $(9_n)$ and then applied to comparators $(12_1)$, $(12_2)$, . . . , $(12_n)$. The amplifiers for the light that has passed the liquid provide outputs about 8 volts, whereas the amplifiers corresponding to the light that has passed the liquid surface (8) provide outputs less than 1 volt.

On the other hand, the standard voltage A set to a certain value is applied to first comparators $(12_1)$, $(12_2)$, . . . , $(12_n)$ from the input terminal (17). This standard voltage A is used to detect the outputs resulting from the light that has passed the liquid surface (8). It may be set to, say, 2 volts. Assume that the liquid surface (8) is projected to small light receiver $(7_m)$ which is hatched in the drawing. The output voltage resulting from this small light receiver is compared by first comparator $(12_m)$ with the standard voltage A supplied from input terminal (17). The comparator is so arranged as to produce an output signal of 0 if the voltage is lower than 2 volts, in other words, if the liquid surface is detected, and to produce an output signal of 1 if the voltage is higher than 12 volts, in other words, if the liquid surface is not detected. Thus, first comparator $(12_m)$ issues a 0 signal and other first comparators $(12_1)$, . . . , $(12_{m-1})$, $(12_m1)$, . . . , $(12_n)$ issue 1 signals, and respective outputs are entered to AND circuits $(13_1)$, . . . , $(13_{m-1})$, $(13_{m+1})$, . . . , $(13_n)$.

On the other hand, not all of outputs from amplifiers $(9_1)$, $(9_2)$, . . . , $(9_n)$ are passed. DC components in the output signals are eliminated by capacitors $(14_1)$, $(14_2)$, . . . , $(14_n)$, and only the signals for detecting foreign matters are passed. In other words, since foreign matters move in the liquid, the outputs from small light receivers $(7_1)$, $(7_2)$, . . . , $(7_m)$ are regarded as AC components. These AC components are amplified by amplifiers $(15_1)$, $(15_2)$, . . . , $(15_n)$ and then applied to second comparators $(16_1)$, $(16_2)$, . . . , $(16_n)$, to which is applied from input terminal (18) the standard voltage B which can be set to a desired value. The standard value B determines the sensitivity for detection of foreign matters. When respective voltages entered from amplifiers $(15_1)$, $(15_2)$, . . . , $(15_n)$ exceed the standard voltage B, second comparators $(16_1)$, $(16_2)$, . . . , $(16_n)$ issue digital signals that indicate that foreign matters are present in excess of the prescribed level. These output signals and the signals entered from first comparators $(12_1)$, $(12_2)$, . . . , $(12_n)$ are applied to AND circuits $(13_1)$, $(13_2)$, . . . , $(13_n)$. If output signal from any one of first comparators $(12_1)$, $(12_2)$, . . . , $(12_n)$ is 0, then there is no output from AND circuits $(13_1)$, $(13_2)$, . . . , $(13_n)$; if output signal from any one of first comparators $(12_1)$, $(12_2)$, . . . , $(12_n)$ is 1, then an output appears at output terminal (19) through corresponding AND circuits $(13_1)$, $(13_2)$, . . . , $(13_n)$.

Light receiver $(7_m)$ corresponding to the liquid surface (8) receives less light and generates a lower voltage than 2 volts of the standard voltage A, causing first comparator $(12_m)$ to issue a 0 output signal.

On the other hand, small light receivers $(7_1)$, . . . , $(7_{m-1})$, $(7_{m+1})$, . . . , $(7_n)$ which do not correspond to liquid surface (8) generate voltages higher than 2 volts, causing first comparators $(12_1)$, $(12_{m-1})$, $(12_{m+1})$, . . . , $(12_n)$ to issue 1 output signals. Therefore, AND circuit $(13_m)$ out of AND circuits $(13_1)$, $(13_2)$, . . . , $(13_n)$ issues no signals regardless of the detection of foreign matters; and other AND circuits $(13_1)$, . . . , $(13_{m-1})$, $(13_{m+1})$, . . . , $(13_n)$ cause second comparators $(16_1)$, . . . , $(16_{m-1})$, $(16_{m+1})$, . . . $(16_n)$ which have detected foreign matters to transmit output signals to output terminal (19) to actuate the solenoid and discharge defective ampoules. In other words, when there is a liquid surface output, the small light receiver corresponding to that is prohibited to issue outputs, but other small light receivers for which there is no liquid surface output and there are foreign matter outputs are allowed to issue outputs.

Small light receivers $(7_1)$, $(7_2)$, . . . , $(7_n)$ may not become dark all, because some of light receivers to which the upper end or lower end of the liquid surface is projected do not become dark completely, even when the rest of light receivers become dark completely due to the projection of the liquid surface. If this occurs in the circuit as shown in FIG. 2, darkening does not take place and inhibition for corresponding light receivers is not effected until the voltage decreases lower than the standard voltage of 2 volts. Such incomplete darkening will be received erroneously as signals for detection of foreign matters, and this might judge acceptable ampoules to be defective. A circuit to prevent such misjudgement and to perform complete inspection is shown in FIG. 3.

Figure 3:
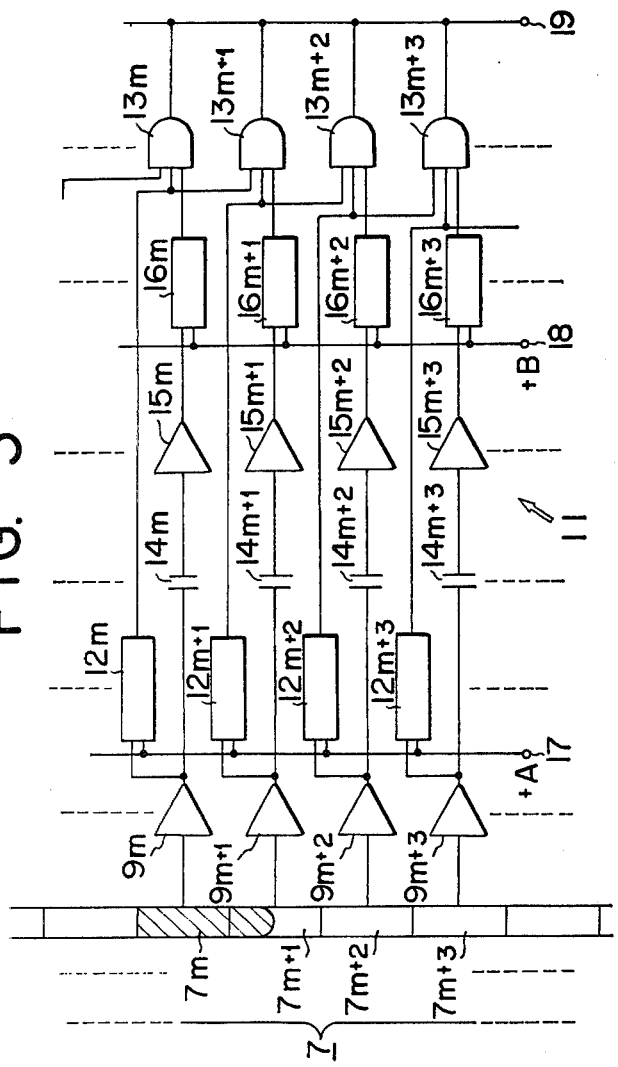
FIG. 3 is a block diagram showing the improved version of the first embodiment.

The difference between the circuits shown in FIG. 2 and FIG. 3 lies in the fact that the outputs from first comparators $(12_1), (12_2), \ldots, (12_n)$ are entered to AND circuits $(13_1), (13_2), \ldots, (13_n)$ connected to adjoining small light receivers. Therefore, if the liquid surface is projected to all of light receivers $(7_m)$ and a part of light receiver $(7_{m+1})$ in the case of the circuit in FIG. 2, the output from first comparator $(12_m)$ becomes 0 signal, but the output from first comparator $(12_{m+1})$ does not become 0 signal because small light receiver $(7_{m+1})$ does not become dark completely and the voltage does not decrease lower than 2 volts. However, in the circuit in FIG. 3, there are three input signals in AND circuits $(13_{m+1})$ and consequently there is no output as long as 0 signal is entered from first comparator $(12_m)$. Therefore, second comparators $(16_m)$ and $(16_{m+1})$ are prevented from issuing outputs. Thus, small light receiver $(7_{m+1})$ adjacent to small light receiver $(7_m)$ which has been darkened completely by the liquid surface $(8)$ is not regarded as one for inspection. This obviates the above-mentioned possibility of misjudgement.

FIG. 3 illustrates an embodiment in which not only the small light receivers which are darkened completely but the small light receiver adjacent to their underside are excluded from those objects for inspection. Based on the same principle, it will be possible to design a circuit in which the small light receiver adjacent to the upperside and lowerside or to the right side and left side is inhibited from issuing output signals for judgement.

In FIG. 3, first comparators $(12_1), (12_2), \ldots, (12_n)$ are connected to AND circuits $(13_1), (13_2), \ldots, (13_n)$ corresponding to the small light receivers adjacent to the upperside, to the upperside and lowerside, or to the right side and left side of small light receivers. For the sake of safety, it will be possible in the same manner to prevent small light receivers adjacent directly to and adjacent but one to the small light receiver which receives the projection of the liquid surface, from issuing an output signal for judgment of rejection.

Incidentally, the area of one section of the small light receiver is designed so that a complete projection of the liquid surface extends over at least one piece of small light receiver.

The other embodiment of this invention will be explained referring to FIG. 4 and FIG. 5.

Figure 4:
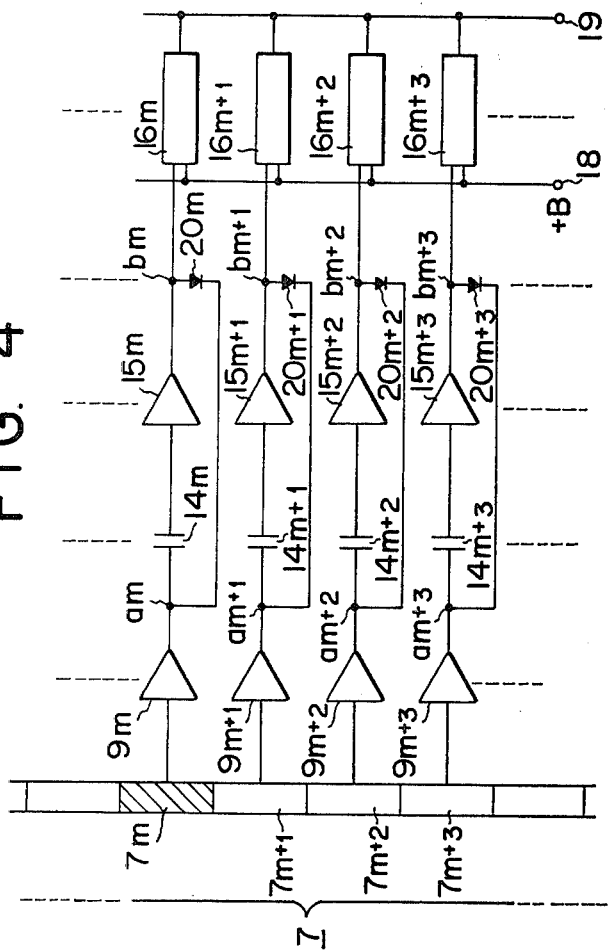
FIG. 4 is a block diagram showing the second embodiment of the apparatus according to this invention.

In FIG. 4, respective outputs from small light receivers $(7_1), (7_2), \ldots, (7_n)$ are sent to amplifiers $(9_1), (9_2), \ldots, (9_n)$. DC components in each output are removed by capacitors $(14_1), (14_2), \ldots, (14_n)$, and only AC components, which are signals for detection of foreign matters, are entered to amplifiers $(15_1), (15_2), \ldots, (15_n)$, and then to comparators $(16_1), (16_2), \ldots, (16_n)$. On the other hand, inhibiting diodes $(20_1), (20_2), \ldots, (20_n)$ are connected in parallel with the AC signal paths between output terminals $(b_1), (b_2), \ldots, (b_n)$ of amplifiers $(15_1), (15_2), \ldots, (15_n)$ and output terminals $(a_1), (a_2), \ldots, (a_n)$ of amplifiers $(9_1), (9_2), \ldots, (9_n)$. To comparators $(16_1), (16_2), \ldots, (16_n)$ is entered the reference voltage B set to a certain level, and it is compared with inputs from amplifiers $(15_1), (15_2), \ldots, (15_n)$. If the inputs are lower than the reference value B, a digital signal representing a defective ampoule appears at output terminal $(19)$.

Now, assume that the small light receiver corresponding to the liquid surface $(8)$ is $(7_m)$. Light receivers $(7_1), \ldots, (7_{m-1}), (7_{m+1}), \ldots, (7_n)$ which receive light passing through the liquid generate lower voltage than light receiver $(7_m)$. Utilizing this phenomenon, amplifiers $(9_1), (9_2), \ldots, (9_n)$ are adjusted so that the voltage of amplifiers $(9_m)$ due to light passing through the liquid surface is, say, $-1$ volt, and the voltage of amplifiers $(9_1), \ldots, (9_{m-1}), (9_{m+1}), \ldots, (9_n)$ resulting from light not passing through the liquid surface, is say, 8 volts. In addition, 0 to 5 volts is set for the output voltage resulting from the foreign matter detection signal from amplifiers $(15_1), (15_2), \ldots, (15_n)$, and the standard voltage B is set to 2 volts. Then, when the liquid surfaces $(8)$ is detected, the output voltage $(a_m)$ from the amplifier $(9_m)$ is lower than the voltage $(b_m)$ of the amplifier $(15_m)$. Consequently, the voltage of $(b_m)$ becomes almost equal to the voltage of $(a_m)$, owing to inhibiting diode $(20_m)$, and comparator $(16_m)$ does not work. In the case of light receivers $(7_1), \ldots, (7_{m-1}), \ldots, (7_{m+1}), \ldots, (7_n)$ except $(7_m)$, as mentioned above, the voltage of diode cathode side $(a_1), \ldots, (a_{m-1}), (a_{m+1}), \ldots, (a_n)$ is higher than the voltage of anode diode side $(b_1), \ldots, (b_{m-1}), \ldots, (b_{m+1}), \ldots, (b_n)$. Therefore, no current flows in diodes $(20_1), \ldots, (20_{m-1}), (20_{m+1}), \ldots, (20_n)$, and they are entered to comparators $(16_1), \ldots, (16_{m-1}), (16_{m+1}), \ldots, (16_n)$. Thus, output signals are issued for light which has passed through the liquid not corresponding to the liquid surface $(8)$.

Some of small light receivers $(7_1), (7_2), \ldots, (7_n)$ become dark completely due to the projection of the liquid surface, but some of them do not become dark completely because the liquid surface is projected to only a part of them. In such a case, there is a possibility that darkening due to the liquid surface is regarded as darkening due to foreign matters. This is prevented by an embodiment as shown in FIG. 5, in which respective output terminals $(a_1), (a_2), \ldots, (a_n)$ of amplifiers $(9_1), (9_2), \ldots, (9_n)$ are connected to adjacent comparators $(16_2), (16_3), \ldots, (16_n)$ through inhibiting diodes $(21_1), (21_2), \ldots, (21_{n-1})$. In such construction, the voltage of the output terminal $(a_{m+1})$ of light receiver $(7_{m+1})$ does not decrease to $-1$ volt when a part of light receiver $(7_{m+1})$ becomes darkened by the liquid surface $(8)$, but the voltage of the output terminal $(a_m)$ of entirely darkened light receiver $(7_m)$ is decreased to $-1$ volts. Consequently, the voltage of the output terminal $(b_{m+1})$ is also decreased to $-1$ volt by diode $(21_m)$, and no signal is entered to comparator $(16_{m+1})$. In this way, not only those light receivers which are darkened completely by the liquid surface but other light receivers adjacent to the darkened light receivers do not issue any signals. Therefore, no mistake occurs in inspection.

Figure 5:
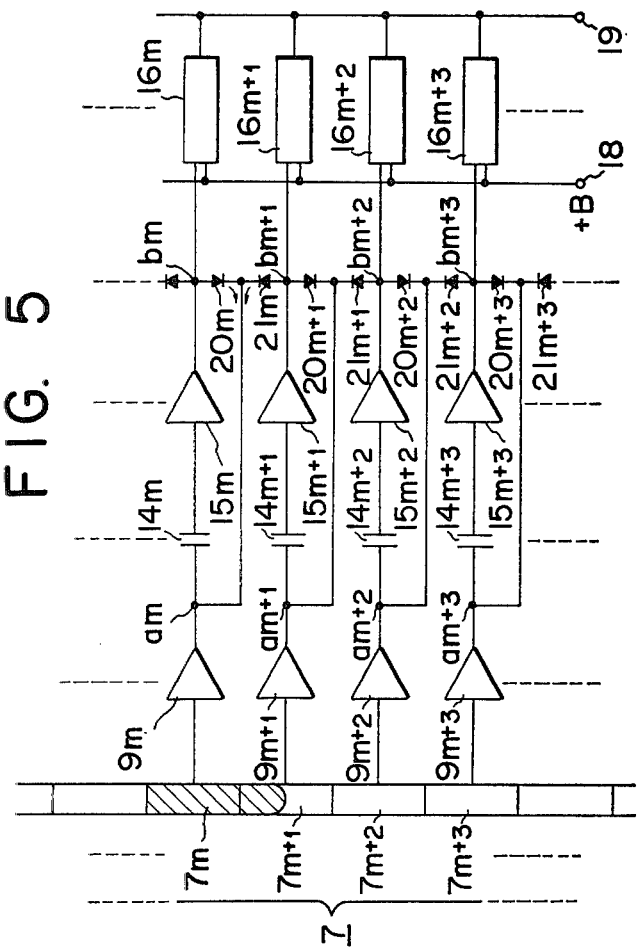
FIG. 5 is a block diagram showing the improved version of the second embodiment.

FIG. 5 illustrates an embodiment in which not only those small light receivers which are darkened completely by the liquid surface $(8)$ but other small light receivers adjacent to the underside of the darkened light receivers are excluded from inspection objects. The same principle may be applied to design a circuit in which the small light receivers adjacent to the upperside, the upperside and lowerside, or the right side and left side of the darkened light receivers are inhibited to issue signals for judgement of rejection.

In such a circuit, respective output terminals $(a_1)$, $(a_2), \ldots, (a_n)$ of amplifiers $(9_1), (9_2), \ldots, (9_n)$ are connected through inversed diodes to comparators $(16_1)$, $(16_2), \ldots, (16_n)$ adjacent to the upperside, the upperside and lowerside, or the right side and left side of them. It is possible to construct the circuit so that more than two adjacent light receivers are inhibited to issue signals for judgement of rejection.

Incidentally, the area of one section of the small light receiver is designed so that the liquid surface is projected to more than one light receiver.

What is claimed is:

1. In an apparatus for detecting foreign matters in liquids by turning at a high speed a transparent container filled with a liquid, bringing the container to a standstill quickly, permitting suspended foreign matters to swirl with the liquid, illuminating the liquid and foreign matters, causing the transmitted light to be received by light receivers of a light detector provided in correspondence with the container, and measuring the change of incident light and transmitted light, the improvement which comprises the light receiver including an aggregate of small light receivers, each of said light receivers being connected to a corresponding unit of a first comparator group which compares the DC signal component obtained from the small light receivers with the standard value arbitrarily set as the signal level for detection of the liquid level to be excluded, each of said small light receivers being connected to a corresponding unit of a second comparator group which compares the AC signal component obtained from the small light receivers with the standard value set as the level for detection of foreign matters, said first comparator group and said second comparator group being connected to a corresponding AND circuit group, whereby said small light receivers are inhibited from issuing an output for judgement of rejection due to an output from one of said small light receivers which corresponds to the liquid surface.

2. The apparatus for detecting foreign matters in liquids as set forth in claim 1, wherein the comparator group for DC signal components and standard value is connected also to AND circuit corresponding to more than one small light receiver.

3. The apparatus for detecting foreign matters in liquids as set forth in claim 1 including an input capacitor in series with an amplifier and therewith comprising an AC coupled amplifier interposed between each light receiver and its corresponding unit of said second comparator group, and a further amplifier connecting each light receiver to both the corresponding said capacitor and the said corresponding unit of said first comparator group.

4. In an apparatus for detecting foreign matters in liquids by turning at a high speed a transparent container filled with a liquid, bringing the container to a standstill quickly, permitting suspended foreign matters to swirl with the liquid, illuminating the liquid and foreign matters, causing the transmitted light to be received by light receivers of a light detector provided in correspondence with the container, and measuring the change of incident light and transmitted light, the improvement which comprises the light receiver including an aggregate of small light receivers, each of said small light receivers being connected to a corresponding amplifier for AC signal components, said amplifier for AC signal components being connected to a comparator group which compares the output of said amplifier with a standard value set according to the level for detection of foreign matters, and said small light receivers being connected to inhibiting diodes connected in parallel with said amplifiers for AC signal components.

5. The apparatus for detecting foreign matters in liquids as set forth in claim 4, wherein further inhibiting diodes are connected between the small light receivers and the comparators which are adjacent to said small light receivers and corresponding to the small light receiver for detecting the liquid surface.

6. The apparatus for detecting foreign matters in liquids as set forth in claim 4, in which said amplifier for AC signal components includes an amplifier with a capacitor in series with the input thereof for blocking DC voltage inputs thereto, said diode connecting at its anode to a point at which the output of said amplifier is led to the corresponding input to the comparator group, said diode connecting at its cathode to a point between the connecting light receiver and capacitor, said diode holding said comparator low when light to the corresponding light receiver is reduced by passing through the liquid surface and thereby preventing said comparator from erroneously signaling as though it has detected a foreign matter in the field of view of the corresponding light receiver.

7. In an improved method for detecting foreign matters in liquids by turning at a high speed a transparent container filled with a liquid, bringing the container to a standstill quickly, permitting the suspended foreign matters to swirl with the liquid, illuminating the liquid and foreign matters, causing the transmitted light to be received by light receivers of a light detector provided in correspondence with the container, and measuring the change of incident light and transmitted light, the improvement which comprises employing as said light receivers an aggregate of small light receivers, each receiver issuing an output signal for a judgement of rejection when the quantity of light received decreases below a certain standard level due to the movement of foreign matters, each receiver issuing an output signal for the liquid level when the quantity of light received decreases below a certain standard level due to the projection on the receiver of the swirling liquid surface formed by the rotation of the liquid, said liquid level signal preventing, for each small light receiver, said signal for a judgement of rejection from being transmitted to the succeeding output terminals.

8. The method for detecting foreign matters in liquids as set forth in claim 7, wherein the small light receivers adjacent to the upperside and lowerside and/or the right side and left side of the small light receiver corresponding to the liquid surface are inhibited to issue an output for judgement of rejection.

* * * * *